United States Patent [19]
Tooley et al.

[11] Patent Number: 5,985,789
[45] Date of Patent: Nov. 16, 1999

[54] RU, SN/OXIDE CATALYST AND PROCESS FOR HYDROGENATION IN ACIDIC AQUEOUS SOLUTION

[75] Inventors: Patricia Ann Tooley, Wilmington, Del.; Jesse Raymond Black, Baton Rouge, La.

[73] Assignee: E. I. du Pont de Nemours and Company, Wilmington, Del.

[21] Appl. No.: 08/828,976

[22] Filed: Mar. 27, 1997

[51] Int. Cl.⁶ .............................. B01J 23/40; B01J 23/42
[52] U.S. Cl. .................... 502/326; 502/352; 549/325; 562/509
[58] Field of Search ................. 502/326, 352; 549/325; 562/509

[56] References Cited

U.S. PATENT DOCUMENTS

| | | | |
|---|---|---|---|
| 4,865,719 | 9/1989 | Moser | 208/139 |
| 5,334,769 | 8/1994 | Ferrero et al. | 568/435 |
| 5,476,827 | 12/1995 | Ferrero et al. | 502/227 |

FOREIGN PATENT DOCUMENTS

| | | |
|---|---|---|
| 0 282 409 | 9/1988 | European Pat. Off. . |
| 5-246915 | 9/1993 | Japan . |
| 6-116182 | 4/1994 | Japan . |
| 6-239778 | 8/1994 | Japan . |
| 7-165644 | 6/1995 | Japan . |
| WO 96/22832 | 8/1996 | WIPO . |

OTHER PUBLICATIONS

Tahara, Chemical Abstracts 125:36263, 1996.
Coq, Chemical Abstracts 121:204647, 1994.
Coq, Chemical Abstracts 120:57122, 1993.
Casreact abstract #123:227624, abstract of JP 07165644, Jun. 1995.
Casreact abstract #122:30951, abstract of JP 06239778, Aug. 1994.
V. M. Deshpande et al., Studies on Ruthenium–Tin Boride Catalysts, *Journal of Catalysis,* 121, 165–173, 1990.
V. M. Deshpande et al., Studies on Ruthenium–Tin Boride Catalysts, *Journal of Catalysis,* 121, 174–182, 1990.
Katsuhiko Tahara et al., Liquid Phase Hydrogenation Of Carboxylic Acid Catalyzed By Supported Bimetallic Ru–Sn–Alumina Catalyst: Effects Of Tin Compounds In Impregnation Method, *Journal of Molecular Catalysis,* 110, L5–L6, 1996.
S. Heinrich et al., Uber Die Bindung In Den Mischungen Fe–Sn UND Ru–Sn, *Journal of the Less–Common Metals,* 52, 87–91, 1977.
T. Massalski, Ru–Sn Phase Diagram, *Binary Alloy Phase Diagrams,* 3, 2nd Edition, 3255 and 3257, 1990.

*Primary Examiner*—D. Margaret M. Mach

[57] ABSTRACT

Improved hydrogenation catalysts consisting essentially of reduced or at least partially reduced ruthenium and tin on a refractory oxide support which is insoluble in aqueous acid. Such catalysts are very durable and exhibit high conversion rates in aqueous acidic solution hydrogenation of hydrogenatable precursors (e.g. maleic acid, succinic acid, gamma-butyrolactone etc.) and high selectivity for their conversion to 1,4-butanediol and gamma-butyrolactone and their mixtures.

4 Claims, No Drawings

RU, SN/OXIDE CATALYST AND PROCESS FOR HYDROGENATION IN ACIDIC AQUEOUS SOLUTION

BACKGROUND OF THE INVENTION

1. Field of the Invention

This invention relates to an improved hydrogenation catalyst, and a method for using the catalyst in a hydrogenation process. More specifically but not by way of limitation the invention relates to the production of 1,4-butanediol and gamma-butyrolactone and mixtures thereof from a hydrogenatable precursor such as maleic acid, succinic acid, their anhydrides, esters, gamma-butyrolactone and mixtures thereof in an acidic aqueous medium in the presence of hydrogen and a catalyst consisting essentially of reduced or at least partially reduced ruthenium and tin on an aqueous acid insoluble refractory oxide support.

2. Description of Related Art

Various methods and reaction systems have been proposed in the past for manufacturing tetrahydrofuran (THF), 1,4-butanediol (BDO) and gamma-butyrolactone (GBL) by catalytic hydrogenation of maleic acid, succinic acid, their anhydrides, esters, and/or related hydrogenatable precursors. Also a variety of hydrogenation catalysts have been historically proposed for this purpose including Group VIII noble metals, combinations of them and also their combinations with rhenium, tin and germanium deposited on various inert supports. These methods and the catalysts described heretofore produce different amounts of a number of hydrogenated products. For example, U.S. Pat. No. 4,609,636 describes the use of a catalyst composite comprising palladium and rhenium on a carbon support for making THF, BDO or mixtures thereof from a variety of hydrogenatable precursors. Also Japanese patent application publications (Kokai) 6-157490, and 6-179667 disclose methods for preparing THF by catalytic hydrogenation of maleic anhydride or maleic acid in the presence of an acidic substance using as a catalyst a rhenium compound and a Group VIII metal. Comparative examples illustrate the use of a catalyst comprising ruthenium and rhenium supported on a carbon support without the acidic substance being present.

Methods are known in the art for the selective production of THF by the catalytic reduction of hydrogenatable precursors. For example, U.S. Pat. No. 4,609,636 teaches that the relative ratio of THF to BDO can be increased by increasing one or more variables selected from operating temperature, contact time, and hydrogen space-time. It is also known from numerous references such as U.S. Pat. No. 3,726,905, that dehydration of BDO to give THF is catalyzed by acid and that increasing the acid concentration results in an increase of the relative ratio of THF to BDO. U.S. Pat. No. 5,478,952 relates to an improved catalyst and method for the production of THF, GBL and BDO by hydrogenation in aqueous solution; the catalyst consisting essentially of highly dispersed, reduced ruthenium and rhenium on a carbon support. THF and GBL are the principal products from this process, THF usually predominating and only minor amounts of BDO and GBL being produced. Japanese patent application publication (Kokai) 5-246915 teaches the use of any Group VIII noble metal, including palladium and ruthenium in combination with either tin, rhenium or germanium as a catalyst for aqueous phase hydrogenation of carboxylic acids or esters. The reference distinguishes the claimed subject matter from previous aqueous phase hydrogenation catalysts incorporating these metals by virtue of specifically claiming the use, as carrier, of porous carbon having a BET surface area of at least 2000 $m^2/g$. The main products which result from this process are THF and GBL. Japanese patent application publication (Kokai) 6-239778 describes the catalytic hydrogenation of maleic acid using supported ruthenium and tin bimetallics. In the examples silica is the support. Titania and zirconia are disclosed also as supports. It is a feature of this catalyst that performance is improved by the addition of alkali metal compounds or nitrogen containing bases. Yields of 30 to 50% BDO are obtained in autoclave reactions with GBL constituting the other major product.

Japanese patent application publications (Kokai) 6-116182 and 7-165644 also relate to the use of ruthenium and tin bimetallics for the catalytic hydrogenation of maleic acid to produce THF, GBL and BDO. In the first reference the preferred support is silica modified with titania or alumina and the highest yield of BDO shown in the examples is 3.5%. Comparative examples are described in which non-modified silica and titania are the supports. In both cases the yield of BDO is below 1%. In the latter reference the addition of platinum and rhodium is also necessary and silica is the only support used in the examples, with titania and silica being disclosed as possible supports. The highest yield of BDO shown in the examples is 15%.

An important area subject to improvement is selectivity with respect to the products of a catalytic hydrogenation process. Selectivity is defined herein to refer to a measure of the percentage of the principal products of a process which in the case of this invention are BDO and GBL. The processes described heretofore do not teach how BDO or GBL or their mixtures can be selectively produced while producing only small amounts of THF, alkanols, carboxylic acids and alkanes as byproducts. The greatly improved selectivity obtained with the process of this invention is of important commercial significance since it allows for the more economical production of BDO and GBL, two commodities with a variety of uses.

Both BDO and GBL can be readily converted to THF which is a widely used solvent in many processes. THF is an excellent solvent for high polymers such as polyvinyl chloride and as a monomer it is used in the production of polyether polyols.

SUMMARY OF THE INVENTION

The present invention provides an improved hydrogenation catalyst possessing exceptional activity, selectivity and durability in an acidic aqueous media at high temperature and pressure, said catalyst consisting essentially of 0.1 to 10 wt % ruthenium and 0.1 to 20 wt % tin supported on a refractory oxide or mixture of oxides, said percentages based on total weight of supported catalyst, wherein said catalyst support is insoluble in acidic aqueous solution at a pH of 1, a temperature up to 300° C. and a pressure up to 35 MPa.

The present invention further provides an improved method for the catalytic hydrogenation of a hydrogenatable precursor in an acidic aqueous solution to produce primarily 1,4 butanediol (BDO), gamma-butyrolactone (GBL) and mixtures thereof comprising the steps of:

a) hydrogenating a hydrogenatable precursor in an acidic aqueous solution in the presence of hydrogen and a catalyst, said catalyst consisting essentially of 0.1 to 10 wt % ruthenium and 0.1 to 20 wt % tin supported on a refractory oxide or mixture of oxides wherein said catalyst support is insoluble in acidic aqueous solution at a pH of 1, a temperature up to 300° C. and a pressure up to 35 MPa, the hydrogenation being conducted at a temperature in the range of 50 to 300° C. and at a pressure in the range of 7 to 35 MPa; and then;

b) recovering BDO and GBL.

Thus, it is an object of this invention to provide a practical process for producing BDO or GBL selectively and economically in higher yield than have been heretofore achieved by the catalytic hydrogenation of suitable precursors in an acidic aqueous medium. More specifically, it is a primary object of the present invention to provide a catalyst system and process conditions that give high conversions of precursors such as maleic acid, succinic acid, their anhydrides, esters and mixtures thereof and gamma-butyrolactone to selectively produce BDO and GBL while forming only minor amounts of THF and other byproducts.

DESCRIPTION OF THE PREFERRED EMBODIMENTS

Catalyst and Preparation

The hydrogenation catalyst according to the present invention involves both ruthenium and tin being present on a refractory oxide support. The catalyst comprises 0.1 to 10 wt % ruthenium and 0.1 to 20 wt % tin based on the total weight of the catalyst. Preferably the catalyst contains 1 to 6% ruthenium and 2 to 10% tin, an especially preferred catalyst has a composition of 2% Ru and 5% Sn based on the total weight of the catalyst due to the combination of activity and selectivity.

It has been found that when the metal components are supported on a material which is highly resistant to aqueous acidic solutions under the severe conditions used in the hydrogenation process the catalyst is very durable and has a long operating life. Refractory oxides are suitable as supports provided they do not promote undesired reactions and are insoluble in the hydrogenation process. Typical examples of suitable supports are titanium oxide and zirconium oxide. Other refractory oxides such as silica and alumina are too soluble in the aqueous acidic medium at the conditions used in the hydrogenation process and this results in severe deterioration of the catalyst and loss of activity thus shortening the effective life of the catalyst. Preferably the catalyst support is a particulate solid characterized with a BET surface area greater than 2 $m^2/g$, typically ranging from about 2 $m^2/g$ to about 300 $m^2/g$. Preferably the refractory oxides will be commercially available material which is commonly supplied in the form of powders, spheres, tablets, extrudates, and the like, which can be crushed and screened to porous aggregates having a size range appropriate to the particular hydrogenation reactor for which they are intended.

The catalyst compositions of this invention can be prepared using solutions of soluble ruthenium and tin compounds and fine powders of the refractory oxide component. For example, a method for preparing said catalyst includes, in sequence, the steps of:

a) impregnating an oxide powder support with solutions containing sources of ruthenium and tin and precipitating the ruthenium and tin as oxides or hydroxides so that they are intermingled with the oxide support;

b) allowing the intermingled oxide support and ruthenium and tin components to age at ambient temperature;

c) removing the solvent by evaporation, preferably while heating, and washing repeatedly with solvent to remove residual traces of soluble impurities;

d) drying the solids; and e) heating the solids in a hydrogen atmosphere at a temperature in the range of 110 to 300° C. for several hours to reduce or at least partially reduce to the metals. It will be appreciated by those skilled in the art that variants of this method can also be used to prepare the catalysts of this invention; for example, the ruthenium and tin can be applied to the support and reduced successively or the final reduction step can be conducted in the hydrogenation reactor. It is preferred to use aqueous solutions of ruthenium and tin salts for reasons of economy, and from the standpoint of toxicity and environmental considerations although useful catalysts can be made using solutions of suitable ruthenium and tin compounds in organic solvents.

Examples of ruthenium compounds which are soluble in water or typical organic solvents and which can be used for preparing the catalyst are ruthenium salts such as ruthenium chloride, ruthenium nitrate, ruthenium nitrosyl nitrate complex etc., organic ruthenium compounds such as ruthenium acetylacetonate, ruthenium chelate complexes, e.g. ruthenium combined with a chelating agent such as ethylenediamine, phenanthroline, bipyridyl, carbonyl ruthenium, ruthenium alkoxide and the like. Preferably ruthenium trichloride is used because of availability and cost advantage.

As to suitable tin compounds examples are tin salts such as stannous chloride, stannous nitrate, sodium stannate, potassium stannate etc., organic tin compounds such as tin octylate and tributyl tin chloride. Preferably stannous chloride is used because of availability and cost advantage.

Catalytic Hydrogenation Process for Producing BDO and GBL

Another aspect of the present invention is the use of the ruthenium/tin/refractory oxide catalyst composition described above to hydrogenate a hydrogenatable precursor to selectively produce BDO and GBL and mixtures thereof, while producing only small amounts of THF, alkanes, alkanols, carboxylic acids and other by products. A preferred aspect of the invention is the selective production of BDO by hydrogenation of maleic acid. Maleic acid is a relatively strong organic acid with a pKa=1.83, similar to perchloric acid with a pKa=1.77. An industrial process for producing BDO from maleic acid requires a support which will withstand the rigors of a strong acidic environment at high temperatures and pressures for a long time and maintain the highest level of catalytic performance over months or years of operation. Many conventional oxide supports such as various types of silica and alumina are too soluble in acidic media to be used as supports to provide suitably long-lived catalysts. The choice of catalytic metals for the hydrogenation of maleic acid to give high yields of BDO is also an important factor. Many catalytic metals such as iron, nickel and chromium undergo corrosive attack under typical reactor conditions. Noble metals of Group VIII are preferred, in particular ruthenium with its propensity for carboxylic finctional group reduction and acid resistance. The incorporation of tin with ruthenium results in increased selectivity for the production of BDO.

The liquid phase hydrogenation of this invention can be run using conventional apparatus and techniques in a stirred-tank reactor or in a fixed-bed reactor operated in a batch, semi-batch, or continuous mode, wherein an acidic aqueous liquid phase containing the hydrogenatable precursor is in contact with a solid catalyst and a gaseous phase containing hydrogen at elevated temperature and pressure. Preferably, the hydrogenation is run in a continuous mode. Hydrogen is fed generally in considerable stoichiometric excess with no inert diluent gases. Unreacted hydrogen can be returned to the reactor as a recycle stream. The precursor solution, e. g., maleic acid solution, is fed continuously at concentrations ranging from dilute solutions to near maximum solubility level, typically about 30 to 40 wt %. The amount of catalyst required will vary widely and is dependent upon a number of factors such as reactor size and design, contact time and the like.

In one embodiment of this invention, high yields of BDO can be obtained by hydrogenation of maleic acid in a fixed bed reactor using the catalyst described herein above. In this embodiment, the overall acidity of the reaction medium is limited in comparison to use of stirred tank reactors wherein yield of BDO may be lowered due to maleic acid induced ring closure to form THF.

In an alternative embodiment, maleic acid can be selectively hydrogenated to GBL in a fixed bed or stirred tank reactor using the catalyst of this invention. Subsequently, the GBL may be recovered, if desired, or alternatively, the GBL can be hydrogenated to BDO in a second reactor. This second reactor can be also be either a fixed bed or stirred tank reactor. Further, the catalyst used in the second hydrogenation can be the catalyst of this invention or other known hydrogenation catalysts known in the art such as supported nickel catalysts, copper catalysts, including copper chromites.

In summary a preferred aspect of the process of the present invention describes the types of reactor, catalyst support and choice of catalytic methods to achieve high conversions of maleic acid and high yields of BDO. The hydrogenation reactions are generally performed at temperatures from about 50° C. to 300° C. and typically from about 200° C. to 250° C. and pressures generally from about 7 to 35 MPa and typically from 7 to 14 MPa.

For the purpose of the invention a hydrogenatable precursor can be, in the broadest sense, any compound or material that can be chemically reduced by hydrogenation or hydrogen up-take. This would include, in particular but not by limitation, various organic compounds containing unsaturated or oxygenated functional groups or both and mixtures thereof, such as but again not limited to maleic acid, maleic anhydride, dimethyl maleate, diethyl maleate, succinic acid, succinic anhydride, dimethyl succinate, diethyl succinate, gamma-butyrolactone and mixtures thereof. Most particularly the acidic aqueous phase catalytic hydrogenation of maleic acid to BDO, GBL and their mixtures is illustrative of the utility of the method according to the present invention. In this regard as illustrated in the examples, it should be appreciated that many products of sequential hydrogenation reactions are also potential hydrogenation precursors and byproducts. For example, in the case of maleic acid in aqueous acidic solution, the rapid addition of hydrogen across the double bond converts maleic acid to succinic acid followed by the slower addition of hydrogen to give successively GBL and BDO. Products other than GBL and BDO include but are not limited to acetic acid, propionic acid, butyric acid, succinic acid, 4-hydroxybutyric acid, ethanol, propanol, butanol, methane, ethane, propane, butane and THF. Examples of intermediate hydrogenation products which can function as precursors for other compounds are succinic acid precursor for 4-hydroxybutyric acid; 4-hydroxybutyric acid precursor for GBL and BDO and GBL or BDO precursors for THF. A novel aspect of the catalyst and process conditions used in the present invention is that although many reactions are possible and could result in a wide diversity of products, the teaching of this invention enables high conversions of the initial hydrogenatable precursors to be achieved together with high selectivity for the production of BDO, GBL and mixtures thereof.

The following examples are presented to more fully demonstrate and further illustrate various individual aspects and advantages of the present invention. They should not be construed as limiting in any way the scope of the invention particularly with respect to the range of properties and applications of the catalyst and the utility of the claimed improved process.

EXAMPLE 1

Titanium dioxide as ⅛" diameter tablets, supplied by Calsicat (division of Mallinkrodt), Erie, PA., were crushed and screened to a 10×18 mesh powder. To 50 g of the powder (S.A. 43.7 $m^2/g$) was added a mixture consisting of 2.06 g of $RuCl_3.xH_2O$, supplied by Strem Chemicals, Newburyport, Mass., 8.00 g of 50% aqueous $SnCl_2$ solution, supplied by Strem Chemicals and 20 ml of water. The mixture was stirred and base treated by the addition of 20 g of a 20% NaOH aqueous solution. The slurry was allowed to age by standing for 3 hours at room temperature and then water was removed by drying overnight under vacuum. The dried solids were washed repeatedly with water on a filter and finally dried at 110° C. under vacuum.

5.17 g (4.8 cc) of the dry solids prepared as above were loaded into a 6 cc Hastelloy C U-tube. The U-tube was heated to 110° C. and pressurized to 14 MPa with hydrogen. Hydrogen flow rate was 200 cc/min. The temperature was maintained at 110° C. for 1 hour and then increased and kept at 300° C. for 3 hours maintaining the pressure at 14 MPa and the hydrogen flow rate at 200 cc/min. The U-tube was cooled to room temperature maintaining a flow of hydrogen which provided an active catalyst having the composition 2 wt % Ru/5 wt % Sn on $TiO_2$.

The U-tube containing the catalyst was used as a fixed bed reactor for hydrogenation of acidic aqueous maleic acid. Acidic aqueous feed stock containing 5 wt % maleic acid, 0.5 wt % acetic acid and 2 wt % dioxane as an internal standard was prepared. A sample of the feed stock was titrated using 0.1 N NaOH to precisely determine the percent acid. The reactor containing the reduced catalyst was heated to 225° C. and pressurized to 14 MPa with hydrogen and the hydrogen flow rate through the reactor was adjusted to 200 cc/min. The feed stock was fed at a rate of 6 cc/hr. The exit flow was collected after gas/liquid separation. The product liquid was titrated using 0.1 N NaOH and the difference between the remaining acidity (in the form of succinic acid) and the original acidity enabled the mol % conversion of maleic acid to be calculated. The product was quantitatively analyzed by gas chromatography. Yield was calculated and expressed as mol %. The results summarized in Table 1 show 98% conversion of maleic acid yielding 80.1 mol % BDO and 8.6 mol % GBL. Byproducts measured, including THF, totaled only 4.7 mol %.

EXAMPLES 2–5

The catalyst composition, preparation and the hydrogenation procedure were the same as in Example 1 but with a range of reactor temperatures and the feed stock flow rates. The conversions of maleic acid and the yields of products were determined as in Example 1. The results are summarized in Table 1. In these examples BDO and GBL were the principal products and the most THF, 6.7 mol %, and byproducts, 7.4 mol %, were formed at the highest temperature, and the lowest feed stock flow rate which corresponds to the longest contact time. The best yields of BDO were obtained at about 225° C. and a flow rate of 6 cc/hr with more GBL than BDO being obtained at the higher flow rate of 12 cc/hr. The highest flow rate, 24 cc/hr resulted in only 3.5% conversion of maleic acid.

EXAMPLES 6–8

The catalyst composition was the same as in Example 1 except in Example 6 the $TiO_2$ support was in the form of a spaghetti extrudate, grade P-25 from Degussa, Ridgefield Park, N.J. having a surface area of 49.3 m$^2$/g; in Example 7 the TiO$_2$ was in the form of ⅛" tablets, from Engelhard Corp., Beachwood, Ohio, calcined at 650° C. and having a surface area of 27.9 m$^2$/g; and in Example 8 the TiO$_2$ was in the form of ⅛" tablets, from Engelhard Corp., calcined at 750° C. and having a surface area of 10.6 m$^2$/g. The catalysts were prepared as described in Example 1 and had the same proportions of components namely 2 wt % Ru/5 wt % Sn on TiO$_2$. The catalysts were evaluated in the hydrogenation of maleic acid by the procedure described in Example 1 and the results are summarized in Table 1. In all cases BDO and GBL were the principal products and with the highest yields being 69.7 mol % and 73.1 mol %, respectively. Catalysts with the highest surface area TiO$_2$ support favored BDO production and more GBL was formed using catalysts with the lower surface area TiO$_2$ support.

area was 12.5 m$^2$/g. A mixture of 50 g of ZrO$_2$ powder, and the Sn and Ru salts was prepared as described in Example 1, except 15 ml of water was used instead of 20 ml. The dry solids were recovered and reduced under hydrogen as described in Example 1 except the reduction temperature was 200° C. for 1 hour followed by 300° C. for 2 hours. The resulting catalyst composition was nominally 2 wt % Ru/5 wt % Sn on ZrO$_2$. The catalyst performance was determined using the procedure described in Example 1 for the hydrogenation of maleic acid. The results summarized in Table 2 show 82% conversion of maleic acid yielding 2.8 mol % BDO and 85.4 mol % GBL. Byproducts including THF, totaled only 2.1 mol %. As in hydrogenations using TiO$_2$ as the support only small amounts of by products were formed. In sharp contrast the same process conditions used in Example 1 where TiO$_2$ was the catalyst support gave 80.1 mol % BDO, demonstrating that the composition of the catalyst support has an unexpected major influence on the relative yields of products from the hydrogenation process.

TABLE 1

Catalyst 2 wt % Ru/5 wt % Sn on TiO$_2$

| Ex. | S.A. m$^2$/g (1) | Temp. °C. | Flow rate cc/hr | Convn mol % | Yield, mol % (2) | | | | |
|---|---|---|---|---|---|---|---|---|---|
| | | | | | BDO | GBL | THF | ROH | RCO$_2$H |
| 1 | 43.7 | 225 | 6  | 98  | 80.1 | 8.6  | 1.7 | 2.9 | 0.1 |
| 2 | 43.7 | 225 | 12 | 88  | 39.3 | 49.1 | 0.7 | 1.1 | 0.2 |
| 3 | 43.7 | 225 | 24 | 3.5 | 1.9  | 2.6  | 0.5 | 0.4 | 0.3 |
| 4 | 43.7 | 200 | 6  | 98  | 65.9 | 23.3 | 0.4 | 2.2 | 0.3 |
| 5 | 43.7 | 250 | 6  | 98  | 65.3 | 10.1 | 6.7 | 7.0 | 0.4 |
| 6 | 43.7 | 225 | 12 | 98  | 69.7 | 26.5 | 0.7 | 2.7 | 0.4 |
| 7 | 27.9 | 225 | 12 | 91  | 39.3 | 56   | 0.8 | 1.6 | 0.9 |
| 8 | 0.6  | 225 | 12 | 89  | 27.1 | 73.1 | 1   | 0.5 | 0.1 |

(1) S.A. = surface area of TiO$_2$.
(2) Molar yield based on maleic acid in feed stock
ROH = C$_3$ + C$_4$ alkanols
RCO$_2$H = C$_3$ + C$_4$ carboxylic acids

EXAMPLE 9

Zirconium dioxide ⅛" tablets calcined at 850° C. in air and supplied by Engelhard Corporation, Beachwood, Ohio, were crushed and screened to 18×35 mesh. The ZrO$_2$ surface

TABLE 2

Catalyst 2 wt % Ru/5 wt % Sn on ZrO$_2$

| Ex. | S.A. m$^2$/g (1) | Temp. °C. | Flow rate cc/hr | Convn mol % | Yield, mol % (2) | | | | |
|---|---|---|---|---|---|---|---|---|---|
| | | | | | BDO | GBL | THF | ROH | RCO$_2$H |
| 9  | 12.5(3) | 225 | 6  | 82 | 2.8  | 84.5 | 0.2 | 1.4 | 0.5 |
| 10 | 12.5(3) | 225 | 12 | 66 | 1.2  | 69.3 | 0.1 | 0.5 | 0.2 |
| 11 | 12.5(3) | 225 | 24 | 57 | 3.4  | 49.2 | 0.3 | 0.3 | 0.3 |
| 12 | 12.5(3) | 200 | 6  | 43 | 0.4  | 50.7 | 0.1 | 0   | 0.1 |
| 13 | 12.5(3) | 250 | 6  | 93 | 24.2 | 71.5 | 2.5 | 2.5 | 1.6 |
| 14 | 49.3(4) | 225 | 12 | 96 | 55   | 37.3 | 1.3 | 2.7 | 0.7 |
| 15 | 46.2(5) | 225 | 12 | 98 | 70.6 | 25.2 | 1.2 | 2.6 | 0.5 |
| 16 | 20.9(6) | 225 | 12 | 82 | 8.4  | 80.2 | 0.4 | 0.3 | 0.5 |

(1) Surface area of ZrO$_2$ support.
(2) Molar yield based on maleic acid in feed stock.
(3) ZrO$_2$ supplied by Engelhard, ⅛" tablets, calcined at 850° C. and crushed and screened to 18 × 35 mesh.
(4) Same as (2), calcined at 600° C.
(5) Same as (2), calcined at 600° C.
(6) Same as (2), calcined at 850° C.
ROH = C$_3$ + C$_4$ alkanols
RCO$_2$H = C$_3$ + C$_4$ carboxylic acids

EXAMPLES 10–13

The catalyst composition, preparation and the hydrogenation procedure were the same as in Example 9 but with a range of reactor temperatures and the feed stock flow rates. The conversion of maleic acid and the amounts of products were determined as in Example 1. The results are summarized in Table 2. In all the examples GBL was the principal product, and the most THF, 2.5 mol %, and byproducts, 4.1 mol %, were formed at the highest temperature and at the slowest feed stock flow rate, corresponding to the longest contact time. The best yields of GBL, 69.3 mol %, were obtained at about 225° C. and a flow rate of 6 cc/hr. The $ZrO_2$ support used in these examples had a relatively low surface area of 12.5 $m^2$/g and the BDO yield was quite low over the complete range of temperature and flow rate.

EXAMPLES 14–16

The catalyst composition was the same as in Example 9 except in Example 14 the $ZrO_2$ support was calcined at 600° C., had a surface area of 49.3 $m^2$/g; in Example 15 the $ZrO_2$ was calcined at 600° C., had a surface area of 46.2 $m^2$/g; and in Example 16 the $ZrO_2$ was calcined at 850° C., had a surface area of 20.9 $m^2$/g. The catalysts were prepared as described in Example 9 and had the same proportions of components namely 2 wt % Ru/5 wt % Sn on $ZrO_2$. The catalysts were evaluated for the hydrogenation of maleic acid by the procedure described in Example 1 and the results are summarized in Table 2. Again in all cases BDO and GBL were the principal products with the highest yields being 70.6 mol % and 80.2 mol %, respectively. Catalysts having the highest surface area $Zro_2$ supports favored BDO production and more GBL was formed using catalysts with the lower surface area $ZrO_2$ supports. The amounts of THF, 0.4 to 1.3 mol %, and byproducts, 0.8 to 3.4 mol %, were small.

EXAMPLE 17

To 10 g of $ZrO_2$ powder, prepared as described in Example 9 was added a mixture containing 2.76 g of ruthenium acetylacetonate (supplied by Strem), 1.6 g of a 50% aqueous solution of $SnCl_2$, 15 ml HCl (1:1 in water) and 5 ml MeOH. The product was dried in air then reduced in flowing $H_2$ at 110° C. for 1 hour and then at 300° C. for 3 hours.

EXAMPLES 18–20

The catalysts were prepared as described in Example 9, except the composition was 7 wt % Ru/5 wt % Sn on $ZrO_2$.

EXAMPLE 21

The catalyst was prepared as described in Example 9, using 30 g of $ZrO_2$, 0.62 g of $RuCl_3 \cdot xH_2O$, 0.96 g of $SnCl_2$ (50% aqueous solution), to provide 1 wt % Ru/1 wt % Sn on $ZrO_2$.

EXAMPLE 22

The catalyst was prepared as described in Example 9, using 50 g of $ZrO_2$, 2.06 g of $RuCl_3 \cdot xH2O$, 8.0 g of $SnCl2$ (50% aqueous solution), to provide 2 wt % Ru/5 wt % Sn on $ZrO_2$.

EXAMPLE 23

Ruthenium acetylacetonate, 0.39 g, was dissolved in THF and deposited on $ZrO_2$. After solvent evaporation, material was dried at 110° C. overnight under vacuum to provide 1 wt % Ru on $ZrO_2$ catalyst. 3 Grams of $SnCl_2$ (50% aqueous solution) was added to the 1 wt % Ru on $ZrO_2$ catalyst. The catalyst was dried at 110° C. then reduced for 3 hours at 300° C.

EXAMPLE 24

Ruthenium acetylacetonate, 1.77 g, was dissolved in MeOH (75 ml) and added to 90 g of $ZrO_2$. The product material was dried overnight at 110° C. under vacuum to provide 0.5 wt % Ru on $ZrO_2$. Di-n-butyltin acetate, 1.12 g, was dissolved in 10 ml of MeOH and deposited on 20 g of the 0.5 wt % Ru on $ZrO_2$ catalyst. The product material was dried overnight at 110° C. then reduced in flowing $H_2$ for 3 hours at 300° C.

The catalysts of Examples 17–24 were tested for hydrogenation following the same procedures in Example 9 but with a range of reactor temperatures and feed stock flow rates. The conversion of maleic acid and the amounts of products were determined as in Example 1. The results are summarized in Table 3.

With the exception of Examples 18–20 where the catalyst was 7 wt % Ru/5 wt % Sn on $ZrO_2$, maleic acid conversions were less than 50 mol % over a range of reactor temperatures from 175° C. to 250° C. and a range of feed stock flow rates from 6 to 24 cc/hr. The lower maleic acid conversions correlate with the lower Ru/Sn ratios in the catalysts with the exception of Example 17. The main product obtained in Examples 17 and 21–24 was GBL with yields from 39.5 to 50.7 mol %. Very little THF, 0 to 0.4 mol %, and byproducts, 0 to 9.2 mol %, were produced. The 7% Ru/5% Sn catalyst gave 98 mol % maleic acid conversion at 225° C. and 6 cc/hr feed stock flow rate and the yield of BDO was very high at 93.6%. Higher temperature, 250° C., and faster feed stock flow 12 cc/hr gave 100% conversion but considerably more THF, 3.7 mol %, and byproducts 23.5 mol %, while BDO yield dropped to 59.3 mol %.

TABLE 3

Catalyst with Range of Ru/Sn on $ZrO_2$ (1)

| | | | Flow | | Yield, mol % (2) | | | | |
|---|---|---|---|---|---|---|---|---|---|
| | | Temp. | rate | Convn | | | | | |
| Ex. | wt % | °C. | cc/hr | mol % | BDO | GBL | THF | ROH | $RCO_2H$ |
| 17 | 7/5 | 180 | 6 | 47 | 2.6 | 47 | 0.4 | 0 | 0 |
| 18 | 7/5 | 225 | 6 | 98 | 93.6 | 5.1 | 0.2 | 1.3 | 0 |
| 19 | 7/5 | 250 | 6 | 100 | 59.3 | 8 | 3.7 | 21.2 | 2.3 |
| 20 | 7/5 | 225 | 12 | 59 | 3.3 | 64.4 | 0 | 0 | 0 |

TABLE 3-continued

Catalyst with Range of Ru/Sn on ZrO$_2$ (1)

| Ex. | wt % | Temp. °C. | Flow rate cc/hr | Convn mol % | Yield, mol % (2) | | | | |
|---|---|---|---|---|---|---|---|---|---|
| | | | | | BDO | GBL | THF | ROH | RCO$_2$H |
| 21 | 1/1 | 175 | 12 | 45 | 5 | 39.7 | 0.1 | 2.2 | 7.0 |
| 22 | 2/5 | 200 | 6 | 45 | 0.4 | 50.7 | 0.1 | 0 | 0.1 |
| 23 | 1/5 | 250 | 24 | 38 | 0.3 | 46.5 | 0.2 | 0 | 0 |
| 24 | 0.5/5 | 250 | 12 | 43 | 0.7 | 39.5 | 0.1 | 0 | 0.7 |

(1) In all cases ZrO$_2$ support was from Engelhard, ⅛" tablets, calcined at 850° C. and crushed and screened to 18 × 35 mesh.
S.A. 12.5 m$^2$/g.
(2) Molar yield based on maleic acid in feed stock.
ROH = C$_3$ + C$_4$ alkanols
RCO$_2$H = C$_3$ + C$_4$ carboxylic acids

EXAMPLE 25

A catalyst containing 2 wt % Ru/5 wt % Sn on TiO$_2$ was prepared following procedures of Example 1. 5.1230 g of this catalyst was loaded into the U-tube reactor as described in Example 1. The catalyst was reduced in flowing H2 at 200° C. for 1 hour and then at 300° C. for 2 hours.

Diethyl maleate and hydrogen were fed to the catalyst. Diethyl maleate was fed neat. Hydrogen flow rate was 200 cc/min. Activity was examined at temperatures of 225° C. and at 250° C.; and at feed rates of 6, 12, and 24 cc/hr. Products were analyzed at 6 cc/hr feed rate at each temperature. All diethyl maleate was consumed. Products formed included diethyl succinate, THF, ethanol, GBL and numerous trans-esterification products.

EXAMPLE 26

A 2 wt % Ru/5 wt % Sn on SiO$_2$ catalyst was prepared following the procedures of Example 1, except using SiO$_2$ instead of TiO$_2$. The catalyst was reduced for 1 hour at 200° C. then reduced for 2 hours at 300° C. The catalyst was tested for hydrogenation at 225° C., 12 cc/hr flow rate of maleic acid as described in Example 1. Conversion was 38.1% with selectivity to BDO of 0.3 mol %, THF of 0.1 mol %, GBL of 39 mol %, ROH of 0.8 mol % (ROH=C$_3$+C$_4$ alkanols. No carboxylic acid products were formed. Analysis of product samples by ICP found 252 ppm Si in the first 24 hour (cumulative) sample and 212 ppm Si in the second 24 hour (cumulative) sample, indicating SiO$_2$ was being lost from the catalyst.

The advantages and benefits of the present invention are believed to be significant and numerous. The catalyst of the instant invention provides a very durable system for the production of BDO and GBL in high yields by the hydrogenation of maleic acid and related precursors in an acidic aqueous medium. The proportions of the catalyst metals Ru and Sn and the TiO$_2$ or ZrO$_2$ supports, together with the reactor temperature and feedstock contact time have been found to be critical in obtaining high yields of BDO or GBL or mixture of both while producing only minor amounts of THF and other byproducts such as alkanes, alkanols and alkyl carboxylic acids. Consequently, the instant catalyst and method of use is amenable to continuous mode long duration commercial operation involving the addition of maleic acid and related precursors as an aqueous acidic solution to a pressurized catalytic reactor and the continuous recovery of BDO and GBL by continuously passing hydrogen through the reaction zone, all of which represent and translate into a significant economic advantage, particularly for contemporary commercial scale production of BDO and GBL.

Having thus described and exemplified the invention with a certain degree of particularity, it should be appreciated that the following claims are not to be so limited but are to be afforded a scope commensurate with the wording of each element of the claim and equivalents thereof.

We claim:

1. A method for catalytic hydrogenation of a hydrogenatable precursor in an acidic aqueous solution comprising the steps of:

(a) hydrogenating a hydrogenatable precursor in an acidic aqueous solution in the presence of hydrogen and a catalyst composition consisting essentially of 0.1 to 10 wt % ruthenium and 0.1 to 20 wt % tin supported on a refractory oxide or mixture of oxides, said percentages based on total weight of supported catalyst, said catalyst support being insoluble in acidic aqueous solution at a pH of 1 and a temperature up to 300° C. and having a surface area of at least 2 m$^2$/g.

(b) recovering at least one hydrogenated product.

2. A method according to claim 1 wherein the catalyst support is selected from the group consisting of titanium dioxide, zirconium dioxide and mixtures thereof.

3. A method according to claim 1 wherein the hydrogenatable precursor is selected from a group consisting of maleic acid, maleic anhydride, fumaric acid, succinic acid, the esters of said acids, gamma-butyrolactone and mixtures thereof; and wherein the products comprise at least 50 mole percent, based on the hydrogenatable precursor, 1,4-butanediol, or gamma-butyrolactone, or mixtures thereof.

4. A method according to claim 3 wherein the hydrogenatable precursor is maleic acid and the catalyst support is selected from the group consisting of titanium dioxide, zirconium dioxide and mixtures thereof.

* * * * *